United States Patent
Coates et al.

(10) Patent No.: US 11,834,435 B2
(45) Date of Patent: Dec. 5, 2023

(54) SSTR4 AGONIST SALTS

(71) Applicant: Eli Lilly and Company, Indianapolis, IN (US)

(72) Inventors: David Andrew Coates, New Palestine, IN (US); David Michael Remick, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 17/944,429

(22) Filed: Sep. 14, 2022

(65) Prior Publication Data

US 2023/0099116 A1    Mar. 30, 2023

Related U.S. Application Data

(60) Provisional application No. 63/243,785, filed on Sep. 14, 2021.

(51) Int. Cl.
    C07D 401/12    (2006.01)

(52) U.S. Cl.
    CPC ........ C07D 401/12 (2013.01); *C07B 2200/13* (2013.01)

(58) Field of Classification Search
    CPC .................. C07D 401/12; C07B 2200/13
    See application file for complete search history.

(56) References Cited

U.S. PATENT DOCUMENTS

| | | | |
|---|---|---|---|
| 6,057,338 A | 5/2000 | Yang et al. | |
| 6,063,796 A | 5/2000 | Yang et al. | |
| 6,159,941 A | 12/2000 | Ankersen et al. | |
| 7,473,787 B2 | 1/2009 | McHardy et al. | |
| 7,741,362 B2 | 6/2010 | Tomperi et al. | |
| 7,902,373 B2 | 3/2011 | Blake et al. | |
| 8,835,472 B2 | 9/2014 | Roth et al. | |
| 8,895,602 B1 | 11/2014 | Nam et al. | |
| 9,133,116 B2 | 9/2015 | Jain et al. | |
| 9,371,282 B2 | 6/2016 | Giovannini et al. | |
| 9,789,082 B2 | 10/2017 | Giovannini et al. | |
| 10,071,974 B2 | 9/2018 | Mazzaferro et al. | |
| 10,166,214 B2 | 1/2019 | Giovannini et al. | |
| 10,183,940 B2 | 1/2019 | Mazzaferro et al. | |
| 10,675,268 B2 | 6/2020 | Giovannini et al. | |
| 2002/0052315 A1 | 5/2002 | Hornik et al. | |
| 2008/0300251 A1 | 12/2008 | Sattigeri et al. | |
| 2009/0247474 A1 | 10/2009 | Xue et al. | |
| 2010/0004339 A1 | 1/2010 | Tomperi et al. | |
| 2012/0083471 A1 | 4/2012 | Townsend et al. | |
| 2014/0005165 A1 | 1/2014 | Nair et al. | |
| 2014/0343065 A1* | 11/2014 | Giovannini .......... C07D 417/12 546/276.7 |

FOREIGN PATENT DOCUMENTS

| | | |
|---|---|---|
| CN | 102675290 A | 9/2012 |
| WO | 2008022994 A1 | 2/2008 |
| WO | 2010/059922 A1 | 5/2010 |
| WO | 2014184275 A1 | 11/2014 |

OTHER PUBLICATIONS

Bastin, et al., "Salt Selection and Optimisation Procedures for Pharmaceutical New Chemical Entities", Organic Process Research & Development, American Chemical Society, US, 4(5): 427-435. 2000.
Gupta, et al., "Salts of Therapeutic Agents: Chemical, Physicochemical, and Biological Considerations", Molecules; 23(7): 1719. 2018.
PCT/US2022/076401—International Search Report—dated Nov. 24, 2022—6 pages.
PCT/US2022/076401—Written Opinion—dated Nov. 24, 2022—7 pages.
N. Kim, et al, "Identification of substituted 4-aminopiperidines and 3-aminopyrrolidines as potent MCH-R1 antagonists for the treatment of obesity", Bioorganic & Medicinal Chemistry Letters 16 (2006), pp. 5545-5450.
Crider, et al, "Somatostatin $sst_4$ Ligands: Chemistry and Pharmacology", Mini-Reviews in Medicinal Chemistry, 2007, vol. 7, No. 3, pp. 213-220.

* cited by examiner

*Primary Examiner* — Timothy R Rozof
(74) *Attorney, Agent, or Firm* — Parker McCrary

(57) ABSTRACT

The present invention relates to specific salts of (1S,5R)-(1α,5α,6α)-N-[1,1-dimethyl-2-[(3-methyl-2-pyridyl)oxy]ethyl]-3-azabicyclo[3.1.0]hexane-6-carboxamide, to pharmaceutical compositions comprising said salts, to methods of using said salts to treat physiological disorders, and to intermediates useful in the synthesis of the salts.

19 Claims, No Drawings

SSTR4 AGONIST SALTS

The present invention relates to novel SSTR4 agonist salts, to pharmaceutical compositions comprising the salts, to methods of using the salts to treat physiological disorders, and to intermediates useful in the synthesis of the salts.

Somatostatin, or somatotropin-release inhibitory factor (SRIF), is a cyclic peptide found in humans. It is produced widely in the human body and acts both systemically and locally to inhibit the secretion of various hormones, growth factors and neurotransmitters. The effects of somatostatin are mediated by a family of G protein-coupled receptors, of which five subtypes are known. These subtypes are divided into two subfamilies, the first comprising SSTR2, SSTR3 and SSTR5 and the second SSTR1 and SSTR4.

Somatostatin is involved in the regulation of processes such as for example cellular proliferation, glucose homeostasis, inflammation, and pain. In this aspect, somatostatin or other members of the somatostatin peptide family are believed to inhibit nociceptive and inflammatory processes via the SSTR4 pathway. A number of further therapeutic areas for SSTR4 agonists have been discussed (for examples see Crider, A; *Mini Rev. Med. Chem.* 2002, 7, 213 and references therein; WO 2010/059922 and references therein).

WO 2014/184275 discloses certain 3-azabicyclo[3.1.0]hexane-6-carboxamide derivatives which are SSTR4 agonists, and which are useful for preventing or treating medical disorders related to SSTR4.

There is a need for alternative solid-state forms of selective SSTR4 agonists with improved stability in excipients and favorable flow and bulk properties for the manufacturing of the active pharmaceutical product and drug products.

Accordingly, the present invention provides a compound of Formula I:

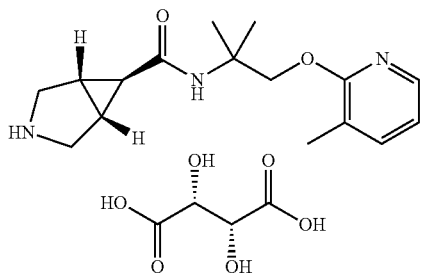

Formula I or a hydrate thereof.

The present invention also provides a compound of Formula I, which is not a hydrate.

The present invention also provides the compound of Formula I, which is a hydrate. The present invention also provides the compound of Formula I, which is a hydrate, wherein the water content at ambient temperature is in the range of 3% to 9% by weight.

The present invention also provides a compound of Formula Ia:

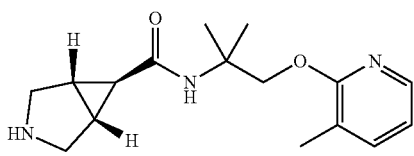

Formula Ia

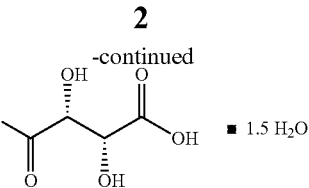

The present invention further provides a compound which is (1S,5R)-(1α,5α,6α)-N-[1,1-dimethyl-2-[(3-methyl-2-pyridyl)oxy]ethyl]-3-azabicyclo[3.1.0]hexane-6-carboxamide L-tartrate sesquihydrate. In addition, the present invention provides a compound which is (1S,5R)-(1α,5α,6α)-N-[1,1-dimethyl-2-[(3-methyl-2-pyridyl)oxy]ethyl]-3-azabicyclo[3.1.0]hexane-6-carboxamide L-tartrate sesquihydrate, which is crystalline.

The present invention also provides a compound of Formula II:

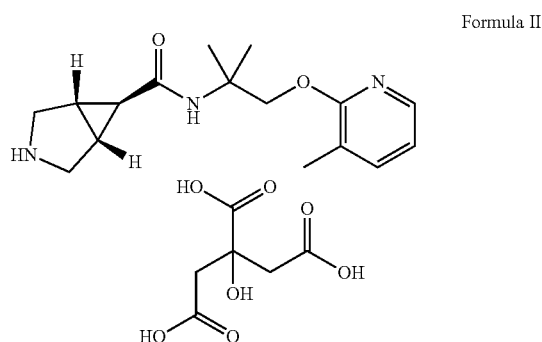

Formula II

The present invention also provides a compound which is (1S,5R)-(1α,5α,6α)-N-[1,1-dimethyl-2-[(3-methyl-2-pyridyl)oxy]ethyl]-3-azabicyclo[3.1.0]hexane carboxamide citrate. In addition, the present invention provides a compound which is (1S,5R)-(1α,5α,6α)-N-[1,1-dimethyl-2-[(3-methyl-2-pyridyl)oxy]ethyl]-3-azabicyclo[3.1.0]hexane-6-carboxamide citrate, which is crystalline.

Furthermore, the present invention provides a compound of Formula III:

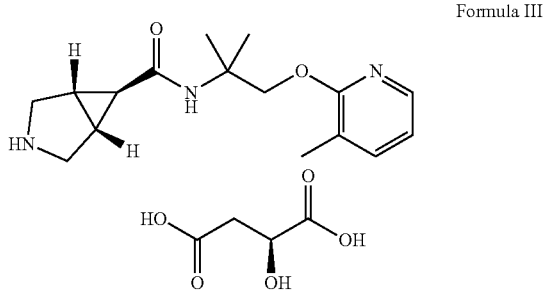

Formula III

In addition, the present invention also provides a compound which is (1S,5R)-(1α,5α,6α)-N-[1,1-dimethyl-2-[(3-methyl-2-pyridyl)oxy]ethyl]-3-azabicyclo[3.1.0]hexane-6-carboxamide L-malate. The present invention further provides a compound which is (1S,5R)-(1α,5α,6α)-N-[1,1-dimethyl-2-[(3-methyl-2-pyridyl)oxy]ethyl]-3-azabicyclo[3.1.0]hexane-6-carboxamide L-malate, which is crystalline.

The present invention provides a crystalline form of a compound of Formula Ia, characterized by an X-ray powder diffraction pattern using CuKα radiation comprising a peak at diffraction angle 2-theta of 15.2°, and one or more peaks at 10.6° and 21.9° (±0.2° respectively).

The present invention also provides a crystalline form of a compound of Formula II characterized by an X-ray powder diffraction pattern using CuKα radiation comprising a peak at diffraction angle 2-theta of 20.8°, and one or more peaks at 10.3°, 16.2° and 5.4° (±0.2° respectively).

The present invention also further provides a crystalline form of a compound of Formula III characterized by an X-ray powder diffraction pattern using CuKα radiation comprising a peak at diffraction angle 2-theta of 18.1°, and one or more peaks at 4.9°, and 17.3° (±0.2° respectively).

The present invention further provides a pharmaceutical composition comprising a compound of Formula I or hydrate thereof, Formula Ia, Formula II, or Formula III with one or more pharmaceutically acceptable carriers, diluents, or excipients. In a particular embodiment, the composition further comprises one or more therapeutic agents.

The present invention provides a method of treating pain in a patient comprising administering to a patient in need of such treatment an effective amount of a compound of Formula I or hydrate thereof, Formula Ia, Formula II or Formula III, or a pharmaceutical composition comprising a compound of Formula I or hydrate thereof, Formula Ia, Formula II, or Formula III with one or more pharmaceutically acceptable carriers, diluents, or excipients. The present invention provides a method of treating chronic back pain, including chronic lower back pain, in a patient comprising administering to a patient in need of such treatment an effective amount of a compound of Formula I or hydrate thereof, Formula Ia, Formula II, or Formula III or a pharmaceutical composition comprising a compound of Formula I or hydrate thereof, Formula Ia, Formula II, or Formula III with one or more pharmaceutically acceptable carriers, diluents, or excipients. The present invention further provides a method of treating neuropathic pain in a patient comprising administering to a patient in need of such treatment an effective amount of a compound of Formula I or hydrate thereof, Formula Ia, Formula II, or Formula III, or a pharmaceutical composition comprising a compound of Formula I or hydrate thereof, Formula Ia, Formula II, or Formula III with one or more pharmaceutically acceptable carriers, diluents, or excipients. In some embodiments, the neuropathic pain is diabetic peripheral neuropathic pain. The present invention also provides a method of treating pain associated with osteoarthritis in a patient comprising administering to a patient in need of such treatment an effective amount of a compound of Formula I or hydrate thereof, Formula Ia, Formula II, or Formula III, or a pharmaceutical composition comprising a compound of Formula I or hydrate thereof, Formula Ia, Formula II, or Formula III with one or more pharmaceutically acceptable carriers, diluents, or excipients.

Furthermore, the present invention provides a compound of Formula I or hydrate thereof, Formula Ia, Formula II, or Formula III, for use in therapy. In addition, this invention provides a compound of Formula I or hydrate thereof, Formula Ia, Formula II, or Formula III for use in the treatment of pain. The present invention also provides a compound of Formula I or hydrate thereof, Formula Ia, Formula II, or Formula III for use in the treatment of chronic back pain, including chronic lower back pain. The present invention further provides a compound of Formula I or hydrate thereof, Formula Ia, Formula II, or Formula III for use in the treatment of neuropathic pain. In some embodiments the neuropathic pain is diabetic peripheral neuropathic pain. The present invention also provides a compound of Formula I or hydrate thereof, Formula Ia, Formula II, or Formula III for use in the treatment of pain associated with osteoarthritis.

In addition, the present invention provides the use of a compound of Formula I or hydrate thereof, Formula Ia, Formula II, or Formula III for the manufacture of a medicament for the treatment of a disease or condition selected from pain, chronic back pain, including chronic lower back pain, neuropathic pain and pain associated with osteoarthritis. In some embodiments the neuropathic pain is diabetic peripheral neuropathic pain.

This invention also encompasses novel intermediates for the synthesis of the compound of Formula I or hydrate thereof, and novel processes for the synthesis of the compound of Formula I or hydrate thereof, Formula Ia, Formula II, and Formula III.

As used herein, the term "hydrate" refers to a solid adduct containing a compound, or a salt thereof, and water, wherein water molecules are incorporated into the crystal lattice of said compound, or salt thereof. As used herein, the term "sesquihydrate" refers to a hydrate of a compound, or salt thereof, wherein the stoichiometric ratio of water to compound, or salt thereof, is 1.5:1.

As used herein, the terms "treating" or "to treat" includes restraining, slowing, stopping, or reversing the progression or severity of an existing symptom or disorder.

As used herein, the term "patient" refers to a mammal, such as a mouse, guinea pig, rat, dog, or human. It is understood that the preferred patient is a human.

As used herein, the term "effective amount" refers to the amount or dose of compound of the invention which, upon single or multiple dose administration to the patient, provides the desired effect in the patient under diagnosis or treatment.

An effective amount can be readily determined by one skilled in the art by the use of known techniques. In determining the effective amount for a patient, a number of factors are considered, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds of the present invention are preferably formulated as pharmaceutical compositions administered by any route which makes the compound bioavailable, including oral route. Most preferably, such compositions are for oral administration. Such pharmaceutical compositions and processes for preparing same are well known in the art (see, e.g., Remington: The Science and Practice of Pharmacy, A. Adejare, Editor, $23^{rd}$ Edition, Elsevier Academic Press, 2020).

The compounds of the present invention may be prepared according to the following Preparations and Examples by methods well known and appreciated in the art. Suitable reaction conditions for the steps of these Preparations and Examples are well known in the art and appropriate substitutions of solvents and co-reagents are within the skill of the art. Likewise, it will be appreciated by those skilled in the art that synthetic intermediates may be isolated and/or purified by various well-known techniques as needed or desired, and that frequently, it will be possible to use various intermediates directly in subsequent synthetic steps with little or no purification. As an illustration, compounds of the preparations and examples can be isolated, for example, by silica gel purification, isolated directly by filtration, or crystallization. Furthermore, the skilled artisan will appreciate that in some circumstances, the order in which moieties are introduced is not critical. The particular order of steps required to produce the compounds of the present invention is dependent upon the particular compound being synthesized, the starting compound, and the relative liability of the substituted moieties, and is well appreciated by the skilled chemist. All substituents, unless otherwise indicated, are as previously defined, and all reagents are well known and appreciated in the art.

Certain abbreviations are defined as follows: "APCI" refers to atmospheric pressure chemical ionization; "BOC" stands for tert-butyloxycarbonyl; "BSA" stands for bovine serum albumin; "cAMP" stands for cyclic adenosine monophosphate; "CTL" stands for control; "DAD" stands for diode-array detection; "DCM" stands for dichloromethane; "DIPEA" stands for N,N-diisopropylethylamine; "DMF" stand for N,N-dimethylformamide; "DMSO" stands for dimethyl sulfoxide; "EDTA" stands for ethylenediaminetetraacetic acid; "EtOAc" stands for ethyl acetate; "HATU" stands for 1-[bis(dimethylamino)methylene]-1H-1,2,3-triazolo[4,5-b]pyridinium-3-oxide hexafluorophosphate; "HBSS" stands for Hank's balanced salt solution; "HEPES" stands for 4-(2-hydroxyethyl)-1-piperazineethane sulfonic acid; "h" stands for hour/s; "HPLC-MS" stands for high performance liquid chromatography mass spectroscopy; "hSSTR" means human somatostatin receptor; "IPA" stands for isopropyl alcohol; "min" stands for minute or minutes; "MS" stands for mass spectroscopy; "IBMX" stands for 1-methyl-3-(2-methylpropyl)-7H-purine-2,6-dione; "m/z" stands for mass to charge ratio; "MTP" stands for microtiter plate; "$R_t$" stands for retention time; "NADPH" stands for dihydronicotinamide adenine dinucleotide phosphate; "RT" stands for room temperature; "rpm" stands for rotations per minute; "TRIS" stands for 2-amino-2-(hydroxymethyl)propane-1,3-diol; "UPLC" stands for ultra-performance liquid chromatography; "v/v" stands for volume by volume.

Scheme 1

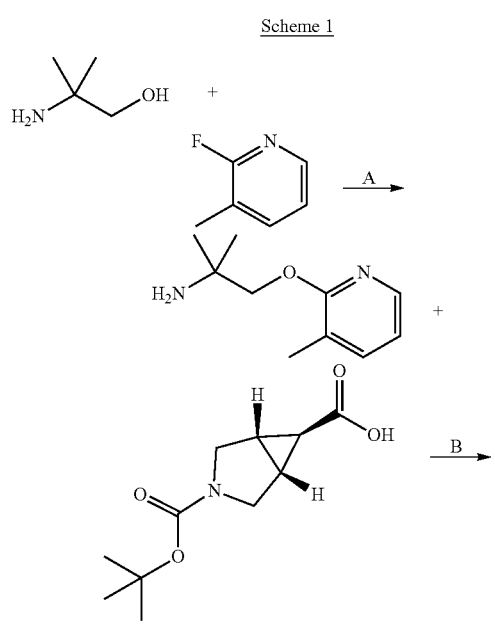

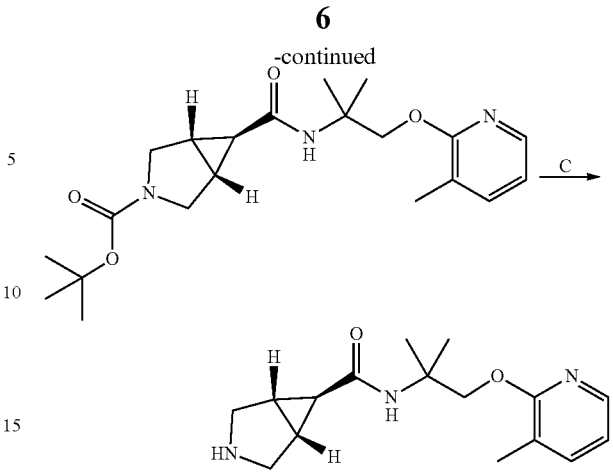

Scheme 1 depicts a general method for the synthesis of (1S,5R)-(1α,5α,6α)-N-[1,1-dimethyl-2-[(3-methyl-2-pyridyl)oxy]ethyl]-3-azabicyclo[3.1.0]hexane-6-carboxamide.

In step A, 2-methylpropan-1-ol is deprotonated using sodium hydride at reduced temperature. The resulting anion is then reacted in situ with 2-fluoro-3-methylpyridine at elevated temperature to yield 2-methyl-1-[(3-methyl-2-pyridyl)oxy]propan-2-amine. The person skilled in the art will recognize that a number of alternative bases could be used for the deprotonation of 2-methylpropan-1-ol, and that, alternatively, the reaction may be performed as a one-pot procedure using milder bases.

In step B, 2-methyl-1-[(3-methyl-2-pyridyl)oxy]propan-2-amine is reacted with (1R,5S,6r)-3-(tert-butoxycarbonyl)-3-azabicyclo[3.1.0]hexane-6-carboxylic acid in the presence of an organic base and the amide coupling reagent HATU to yield tert-butyl (1R,5S,6r)-6-((2-methyl-1-(3-methylpyridin-2-yl)oxy)propan-2-yl)carbamoyl)-3-azabicyclo[3.1.0]hexane-3-carboxylate. The person skilled in the art will recognize that a multitude of different amide coupling reagents and organic bases may be used to achieve this amide formation.

In final step C, tert-butyl (1R,5S,6r)-6-((2-methyl-1-((3-methylpyridin-2-yl)oxy)propan-2-yl)carbamoyl)-3-azabicyclo[3.1.0]hexane-3-carboxylate is subjected to a BOC-deprotection using microwave irradiation in a mixture of methanol and water at elevated temperature to yield (1S,5R)-(1α,5α,6α)-N-[1,1-dimethyl-2-[(3-methyl-2-pyridyl)oxy]ethyl]-3-azabicyclo[3.1.0]hexane-6-carboxamide. The person skilled in the art will be aware of numerous alternative methods to perform a BOC deprotection. A comprehensive list of such methods can be found, for example, in Wuts, P. G. M. and Greene, T. W. (2006), *Protective groups in organic synthesis*, Hoboken, N.J.: Wiley.

LC-MS Method 1

Instrument: LC/MS Thermo Scientific™ Finnigan, HPLC Surveyor DAD, MSQ Plus™ single quadrupole; column: Synergi™ Hydro-RP 100 Å, 2.5 µm, 3×50 mm; mobile phase: A=H$_2$O 90%+10% CH$_3$CN+NH$_4$COOH 10 mM, B=CH$_3$CN 90%+H$_2$O 10%+NH$_4$COOH 10 mM; gradient: 0.0 min 0% B→4.00 min 100% B→5.30 min 100% B→5.50 min 0% B→6.00 min 0% B; flow rate: 1.2 mL/min; detection: UV 254 nm; ion source: APCI+/APCI−.

LC-MS Method 2

LC-MS method 2: Instrument: LC/MS Waters Acquity® UPLC System DAD, SQD single quadrupole; column: BEH C18 1.7 µM 2.1×50 mm, Temp 35° C.; mobile phase: A=H$_2$O 90%+10% CH$_3$CN+NH$_4$COOH 5 mmol, B=CH$_3$CN 90%+H$_2$O 10%; gradient: 0.0 min 0% B→1.20 min 100% B→1.45 min 100% B→1.55 min 0% B→1.75 min 0% B; flow rate: 0.70 mL/min; detection: UV 254 nm; detection: SQD single quadrupole; ion source: ES+/ES−; scan range: 90-900 amu.

Preparation 1

2-Methyl-1-[(3-methyl-2-pyridyl)oxy]propan-2-amine

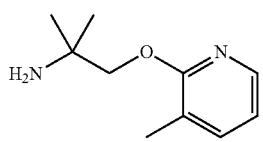

2-Amino-2-methyl-propan-1-ol (11 mL, 118.8 mmol) is dissolved in dioxane (20 mL) and sodium hydride (60% suspension in mineral oil, 5.0 g, 124.7 mmol) is added portion wise at 0° C. and after 15 min 2-fluoro-3-methyl-pyridine (3 mL, 29.7 mmol) is added. The resulting mixture is heated at 100° C. for 1 h. The reaction is diluted with DCM and washed with water. The organic layer is separated, dried, and evaporated under reduced pressure to furnish the title compound (5.1 g, 95%) that is used as such. HPLC-MS (Method 1): R$_t$=1.78 min, MS (APCI): m/z=181 (M+H)$^+$.

Preparation 2 tert-Butyl (1R,5S,6r)-6-((2-methyl-1-((3-methylpyridin-2-yl)oxy)propan-2-yl)carbamoyl)-3-azabicyclo[3.1.0]hexane-3-carboxylate

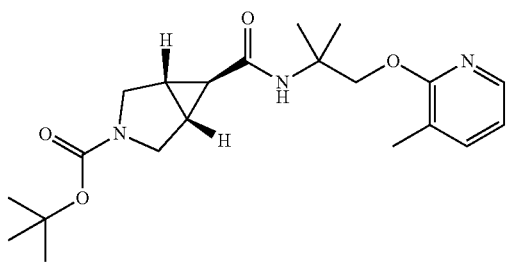 [SMILES: Cc1cccnc1OCC(C)(C)NC(=O)[C@H]1[C@@H]2CN(C(=O)OC(C)(C)C)C[C@@H]21]

2-Methyl-1-[(3-methyl-2-pyridyl)oxy]propan-2-amine (5.1 g, 28.3 mmol), HATU (10.8 g, 28.3 mmol) and DIPEA (15.5 g, 56.589 mmol) are added to (1R,5S,6r)-3-(tert-butoxycarbonyl)-3-azabicyclo[3.1.0]hexane-3-carboxylic acid (6.4 g, 28.3 mmol) (commercially available from ACBR or WuXi AppTec) in DMF (10 mL) and stirring is continued for 3 h. Volatiles are evaporated under reduced pressure. EtOAc is added and the reaction mixture is washed with NaHCO$_3$ saturated solution and then with brine. The organic layer is separated by phase separator cartridge and solvent evaporated affording a residue that is purified by flash chromatography (eluent 20-50% EtOAc/cyclohexane) to furnish the title compound (8.4 g, 76%). HPLC-MS (Method 1): R$_t$=3.30 min, MS (APCI): m/z=390 (M+H)$^+$.

Preparation 3

(1S,5R)-(1α,5α,6α)-N-[1,1-Dimethyl-2-[(3-methyl-2-pyridyl)oxy]ethyl]-3-azabicyclo[3.1.0]hexane-6-carboxamide

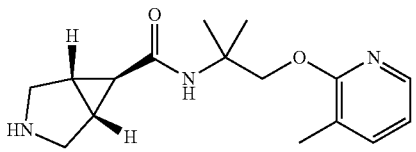 [SMILES: Cc1cccnc1OCC(C)(C)NC(=O)[C@H]1[C@@H]2CNC[C@@H]21]

tert-Butyl (1R,5 S,6r)-6-((2-methyl-1-((3-methylpyridin-2-yl)oxy)propan-2-yl)carbamoyl)-3-azabicyclo[3.1.0]hexane-3-carboxylate (13 g, 33.4 mmol) is suspended in methanol/water 1:1 v/v (35 mL/35 mL), split in 7 equal batches and heated under microwave irradiation (150° C.) for 70 min. Solvents are removed under reduced pressure to give a residue that is purified by flash chromatography (eluent 100% DCM to 93:7:0.7 DCM/methanol/NH$_3$) to furnish the title compound (7.0 g, 72%). LC-MS (Method 2): R$_t$=0.68 min, MS (ESI pos): m/z=290 (M+H)$^+$.

Preparation 4

(1S,5R)-(1α,5α,6α)-N-[1,1-Dimethyl-2-[(3-methyl-2-pyridyl)oxy]ethyl]-3-azabicyclo[3.1.0]hexane-6-carboxamide L-tartrate

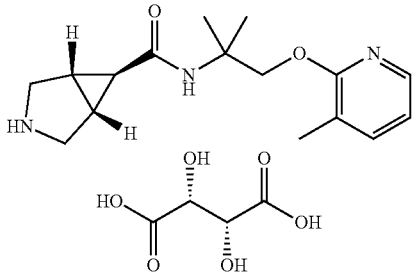

To (1S,5R)-(1α,5α,6α)-N-[1,1-Dimethyl-2-[(3-methyl-2-pyridyl)oxy]ethyl]-3-azabicyclo[3.1.0]hexane-6-carboxamide (5.5 g, 18.4 mmol) is added IPA (68 mL) and water (2 ml). The mixture is heated to 65° C., at which point dissolution occurs. L-Tartaric acid (2.86 g, 19.1 mmol) in IPA (34 mL) and water (1.5 mL) are then added to the solution. The solution is then allowed to cool to RT overnight. The resulting white solid is isolated by vacuum filtration and is rinsed with ice-cold IPA (20 mL) to give the title compound (5.7 g, 70%).

EXAMPLE 1

Crystalline (1S,5R)-(1α,5α,6α)-N-[1,1-dimethyl-2-[(3-methyl-2-pyridyl)oxy]ethyl]-3-azabicyclo[3.1.0]hexane-6-carboxamide L-tartrate sesquihydrate

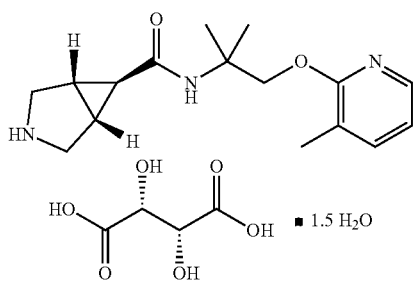

(1S,5R)-(1α,5α,6α)-N-[1,1-Dimethyl-2-[(3-methyl-2-pyridyl)oxy]ethyl]-3-azabicyclo[3.1.0]hexane-6-carboxamide L-tartrate (60 g, 136.5 mmol) is transferred into a 250 mL reactor vessel and THF/water 95:5 v/v is added to a volume of 225 mL. The mixture is heated to 60° C. and water is added in 1 mL aliquots to fully dissolve the starting material (total 8 mL of water). The reactor is allowed to cool naturally, and the mixture is allowed to stir at RT over the weekend. The resulting crystals are isolated by vacuum filtration and air-dried for several days. The resulting solid is sieved to give the title compound (42.3 g, 66%).

EXAMPLE 2

Crystalline (1S,5R)-(1α,5α,6α)-N-[1,1-dimethyl-2-[(3-methyl-2-pyridyl)oxy]ethyl]-3-azabicyclo[3.1.0]hexane-6-carboxamide citrate

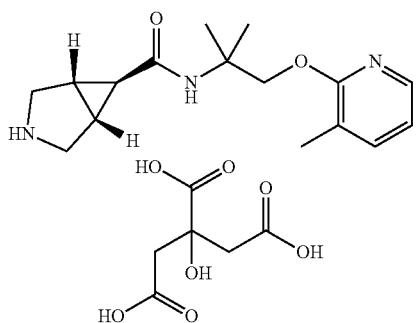

(1S,5R)-(1α,5α,6α)-N-[1,1-Dimethyl-2-[(3-methyl-2-pyridyl)oxy]ethyl]-3-azabicyclo[3.1.0]hexane-6-carboxamide (10.8 g, 33 mmol) is dissolved in absolute ethanol (200 mL) while stirring at 300 rpm at 60° C. This solution is filtered through a 0.65 μm nylon filter to yield a clear solution. The solution is stirred for 5 min upon which solid precipitation occurs. A solution of citric acid (7.06 g, 36 mmol) dissolved in absolute ethanol (60 mL) at 60° C. is prepared. The citric acid solution is added slowly at 60° C. The mixture is filtered through a 0.45 μm syringe filter maintained at 60° C. Heating is then terminated and the mixture is stirred at 500 rpm, gradually cooled to RT. Upon complete equilibration to RT, a very thick white slurry (cake) is obtained. The flask is rinsed with absolute ethanol (5×10 mL) to rinse the cake. The cake solid is isolated on a nylon membrane under vacuum, dried under nitrogen, then overnight at 70° C. under vacuum to give the title compound as a white solid (16.8 g, 98%).

EXAMPLE 3

Crystalline (1S,5R)-(1α,5α,6α)-N-[1,1-dimethyl-2-[(3-methyl-2-pyridyl)oxy]ethyl]-3-azabicyclo[3.1.0]hexane-6-carboxamide L-malate

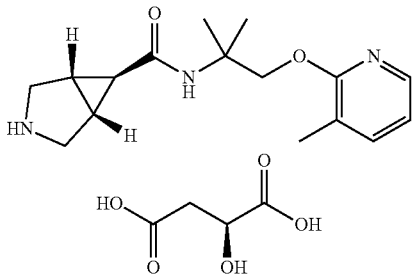

(1S,5R)-(1α,5α,6α)-N-[1,1-Dimethyl-2-[(3-methyl-2-pyridyl)oxy]ethyl]-3-azabicyclo[3.1.0]hexane-6-carboxamide (25 g, 88 mmol) is added to 100 mL of isopropanol while stirring at ~400 rpm. The sample is heated to 60° C. 14.6 mL of L-malic acid solution in water (109 mmol) is then added. A clear yellowish solution is formed. The solution is cooled to RT. Oiling is observed, so the phase separation is evaporated to dryness under nitrogen stream. The solid residue is suspended in acetone and water for a recrystallization at 55° C. The 25 g freebase equivalent material is recrystallized in 200 ml of acetone and 15 mL of water (total 215 mL solvent). The solid is isolated from the reactor vessel at RT using a Buchner funnel under reduced pressure. The white cake is rinsed with acetone and dried at 50° C. under vacuum to give the title compound (21 g, 57%).

X-Ray Powder Diffraction (XRPD) Method 1

The XRPD patterns of crystalline solids are obtained on a Bruker D8 Endeavor X-ray powder diffractometer, equipped with a CuKα (1.5418 Å) source and a Lynxeye™ detector, operating at 40 kV and 40 mA. The sample is scanned between 4 and 42 2θ°, with a step size of 0.009 2θ° and a scan rate of 0.5 seconds/step, and using 0.3° primary slit opening, and 3.9° PSD opening. The dry powder is packed on a quartz sample holder and a smooth surface is obtained using a glass slide. The crystal form diffraction patterns are collected at ambient temperature and relative humidity. Crystal peak positions are determined in MDI-Jade after whole pattern shifting based on an internal NIST 675 standard with peaks at 8.853 and 26.774 2θ°. It is well known in the crystallographic art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g. The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature at which a sample is analyzed, sample displacement, or the presence or absence of an internal standard. In the present case, a peak position variability of ±0.2 2θ° is presumed to take into account these potential variations without hindering the unequivocal identification of the indicated crystal form. Confirmation of a crystal form may be made based on any unique combination of distinguishing peaks.

X-Ray Powder Diffraction (XRPD) Method 2

The XRPD patterns of crystalline solids are obtained on a Bruker D4 Endeavor X-ray powder diffractometer, equipped with a CuKα (1.5418 Å) source and a Vantec™ detector, operating at 35 kV and 50 mA. The sample is scanned between 4 and 40 2θ°, with a step size of 0.008 2θ° and a scan rate of 0.5 seconds/step, and using 1.0 mm divergence, 6.6 mm fixed anti-scatter, and 11.3 mm detector slits. The dry powder is packed on a quartz sample holder and a smooth surface is obtained using a glass slide. The crystal form diffraction patterns are collected at ambient temperature and relative humidity. Crystal peak positions are determined in MDI-Jade after whole pattern shifting based on an internal NIST 675 standard with peaks at 8.853 and 26.774 2θ°. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g. The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature at which a sample is analyzed, sample displacement, or the presence or absence of an internal standard. In the present case, a peak position variability of ±0.2 2θ° is presumed to take into account these potential variations without hindering the unequivocal identification of the indicated crystal form. Confirmation of a crystal form may be made based on any unique combination of distinguishing peaks.

XRPD of Example 1

XRPD method 1 was used for Example 1. A prepared sample of Example 1 is characterized by an XRPD pattern using CuKα radiation as comprising diffraction peaks (2-theta values) as described in Table 1 below, and in particular comprising a peak at diffraction angle 2-theta of 15.2° and one or more of peaks at 10.6° and 21.9°; with a tolerance for the diffraction angles of 0.2 degrees.

TABLE 1

X-ray powder diffraction peaks of Example 1

Example 1

| Peak | Angle (°2-Theta) ± 0.2° | Relative Intensity (% of most intense peak) |
|---|---|---|
| 1 | 8.2 | 9.6% |
| 2 | 10.6 | 16.3% |
| 3 | 12.6 | 11.1% |
| 4 | 12.9 | 13.7% |
| 5 | 13.5 | 18.9% |
| 6 | 14.6 | 21.2% |

TABLE 1-continued

X-ray powder diffraction peaks of Example 1

Example 1

| Peak | Angle (°2-Theta) ± 0.2° | Relative Intensity (% of most intense peak) |
|---|---|---|
| 7 | 15.0 | 39.0% |
| 8 | 15.2 | 100.0% |
| 9 | 15.8 | 26.4% |
| 10 | 16.2 | 22.9% |
| 11 | 16.5 | 8.5% |
| 12 | 17.6 | 39.6% |
| 13 | 17.9 | 30.5% |
| 14 | 18.4 | 40.7% |
| 15 | 18.6 | 21.2% |
| 16 | 19.5 | 46.8% |
| 17 | 20.7 | 15.0% |
| 18 | 21.3 | 33.3% |
| 19 | 21.9 | 77.4% |
| 20 | 22.9 | 27.3% |

XRPD of Example 2

XRPD method 2 was used for Example 2. A prepared sample of Example 2 is characterized by an XRPD pattern using CuKα radiation as comprising diffraction peaks (2-theta values) as described in Table 2 below, and in particular comprising a peak at diffraction angle 2-theta of 20.8° and one or more of peaks at 10.3°, 16.2° and 5.4°, with a tolerance for the diffraction angles of 0.2 degrees.

TABLE 2

X-ray powder diffraction peaks of Example 2

Example 2

| Peak | Angle (°2-Theta) ± 0.2° | Relative Intensity (% of most intense peak) |
|---|---|---|
| 1 | 5.4 | 53.70% |
| 2 | 8.1 | 11.00% |
| 3 | 9.1 | 9.70% |
| 4 | 10.3 | 60.00% |
| 5 | 16.2 | 56.40% |
| 6 | 19.9 | 22.40% |
| 7 | 20.8 | 100.00% |
| 8 | 21.5 | 14.00% |
| 9 | 22.1 | 21.10% |
| 10 | 24.5 | 42.80% |

XRPD of Example 3

XRPD method 2 was used for Example 3. A prepared sample of Example 3 is characterized by an XRPD pattern using CuKα radiation as comprising diffraction peaks (2-theta values) as described in Table 3 below, and in particular comprising a peak at diffraction angle 2-theta of 18.1° and one or more of peaks at 4.9° and 17.3°, with a tolerance for the diffraction angles of 0.2 degrees.

TABLE 3

X-ray powder diffraction peaks of Example 3

| | Example 3 | |
|---|---|---|
| Peak | Angle (°2-Theta) ± 0.2° | Relative Intensity (% of most intense peak) |
| 1 | 4.9 | 72.10% |
| 2 | 14.9 | 100.00% |
| 3 | 16.9 | 6.40% |
| 4 | 17.3 | 11.00% |
| 5 | 18.1 | 33.70% |
| 6 | 19.3 | 10.90% |
| 7 | 19.7 | 18.90% |
| 8 | 20.6 | 17.70% |
| 9 | 21.0 | 4.70% |
| 10 | 23.9 | 15.00% | cAMP Assay

The activation of the SSTR4 receptor (G coupled) causes an inhibition of intracellular cAMP after stimulation with Forskolin, which can be quantifiable by use of a suitable assay Kit and an adequate plate reader. This technique is used to characterize pharmacological effects of the SSTR4 receptor agonists by use of hSSTR4 expressing H4 cells. The compound is dissolved and diluted in DMSO. The final test solution contains 1% DMSO. The cAMP standard (Lance™ cAMP 384 Kit; PerkinElmer, Cat #AD0264) is prepared in assay buffer (HBSS with 0.1% BSA, 5 mM HEPES, 0.5 M IBMX, pH 7.4) containing 1% DMSO and the cAMP standard curve is included at least on one plate. Cells are centrifuged and suspended in assay buffer (incl. 1:100 diluted Alexa Fluor® antibody). For the assay 5 µL of a cell suspension (approximately 5000 cells/well)-incl. Alexa Fluor® antibody (diluted 1:100) are added into a 384 well MTP microtiter plate excepting one row or column (depending on the plate layout), which is reserved for the standard curve. Then 2 µL of compound sample is added as concentration response curve (e.g., 1e-5 M to 6e-10 M), usually in triplicates. Each assay contains incubations with vehicle controls instead of compound as controls for non-inhibited cAMP generation (100% CTL; 'high values') and incubations with 1 µM Somatostatin as controls for full inhibition and background (0% CTL; 'low values'). After approximately 10-15 min incubation time 3 µL Forskolin (dissolved in DMSO, final conc. 15 µM) is added. Then the plates are shaken briefly and incubated for 60 min at RT. After 60 min 10 µL of the detection mix is added into all wells followed by an additional incubation period of 1 h. The plates are read in a suitable plate reader. The analysis of the data is based on the "ratio" of the time-resolved fluorescence measurements of donor and acceptor fluorophore (Ex: 320 nm; Em1: 665 nm; Em2: 615 nm; ratio 665/615). From this ratio, cAMP concentrations are calculated from standard curve and the $EC_{50}$ is estimated by least square curve fit program. The free base of Examples 1, 2 and 3 is tested essentially as described above.

TABLE 4

$EC_{50}$ of Examples 1, 2 and 3 (free base)

| Example | SSTR4 agonism $EC_{50}$ (nM) |
|---|---|
| 1, 2 and 3 (free base) | 3.7 |

As shown in Table 4, Examples 1, 2 and 3, after being dissolved to their free base forms, are agonists of SSTR4.

Selectivity

In competition experiments, the test compound, which is not labeled, competes with the binding site of a labeled ligand. The displacement of the labeled ligand by the test compound leads to a decreased signal. For the binding experiments 200 µL of membrane homogenate from one of the following protein amounts is used: hSSTR1 (40 µg/well); hSSTR2 (25 µg/well); hSSTR3 (1.5 µg/well); hSSTR4 (0.5 µg/well); hSSTR5 (25 µg/well). The homogenate is incubated with 0.05 nM of radioligand ([3-125I-Tyr]-Somatostatin-(1-14)) in addition to increasing concentrations of a test compound or vehicle (100% binding) in a total volume of 250 µL using a Hepes buffer (10 mM, EDTA 1 mM, $MgCl_2$ 5 mM, pH 7.6, BSA 0.5%, Bacitracin 0.003%, DMSO 1%) for 180 min at RT. The incubation is terminated by filtration with ice cold NaCl 0.9% through polyethyleneimine treated (0.3%) grade GF/B glass fiber filters using a cell harvester. The protein-bound radioactivity is measured in a suitable reader. The non-specific binding is defined as radioactivity bound in the presence of 1 µM Somatostatin-14 during the incubation period. The analysis of the concentration-binding curves is performed by computer-assisted nonlinear least square curve fitting method using the model of one receptor binding site.

TABLE 5

Selectivity of Examples 1, 2 and 3 (free base)

| Example | SSTR4 binding $K_i$ (nM) | SSTR1 binding $K_i$ (nM) | SSTR2 binding $K_i$ (nM) | SSTR3 binding $K_i$ (nM) | SSTR5 binding $K_i$ (nM) |
|---|---|---|---|---|---|
| 1, 2 and 3 (free base) | 39.9 | >9148 | >9603 | >8618 | >9863 |

As shown in Table 5, Examples 1, 2 and 3, after being dissolved to their free base forms, selectively bind to SSTR4 over SSSTR1, SSSTR2, SSSTR3 and SSSTR5.

Stability Study

Prototype tablets of (1S,5R)-(1α,5α,6α)-N-[1,1-dimethyl-2-[(3-methyl pyridyl)oxy]ethyl]-3-azabicyclo[3.1.0]hexane-6-carboxamide (Tablet A), Example 1 (Tablet B) and Example 3 (Tablet C) were prepared with the formulations shown in Tables 6, 7 and 8 respectively.

TABLE 6

Formulation of Tablet A

| Material | % w/w |
|---|---|
| (1S,5R)-(1α,5α,6α)-N-[1,1-dimethyl-2-[(3-methyl-2-pyridyl)oxy]ethyl]-3-azabicyclo[3.1.0]hexane-6-carboxamide | 50.00 |
| Microcrystalline cellulose | 42.00 |
| Croscarmellose sodium | 5.00 |
| Sodium stearyl fumarate | 3.00 |
| Total | 100 |

TABLE 7

| Formulation of Tablet B | |
| --- | --- |
| Material | % w/w |
| Example 1 | 65.00 |
| Microcrystalline cellulose | 26.50 |
| Croscarmellose sodium | 5.00 |
| Sodium stearyl fumarate | 3.50 |
| Total | 100 |

TABLE 8

| Formulation of Tablet C | |
| --- | --- |
| Material | % w/w |
| Example 3 | 65.00 |
| Microcrystalline cellulose | 26.50 |
| Croscarmellose sodium | 5.00 |
| Sodium stearyl fumarate | 3.50 |
| Total | 100 |

The tablets were subjected to stability testing according to ICH guidelines using accelerated storage conditions (40° C./75% RH) for 1, 2-, 4-, 8- and 12-week periods).

For chromatographic analysis, one tablet is dissolved in 50/50 mobile phase A/mobile phase B (see HPLC chromatography conditions below) to obtain a sample concentration of about 0.2 mg/mL as (1S,5R)-(1α,5α,6α)-N-[1,1-dimethyl-2-[(3-methyl-2-pyridyl)oxy]ethyl]-3-azabicyclo[3.1.0]hexane-6-carboxamide (free base). The sample is then analyzed by HPLC chromatography (XBridge™ BEH C18, 2.5 μm, 4.6 mm×75 mm I.D; mobile phase: A=H$_2$O 99.9%+0.1% TFA, B=99.9% CH$_3$CN+0.1% TFA; gradient: 0.0 min 5% B→12.1 min 70% B→13.0 min 95% B→16.0 min 95% B 16.1 min 5% B→20.0 min 5% B; flow rate: 1.5 mL/min; column temperature: 30° C.; detection: UV 220 nm; injection volume: 10 μL; autosampler temperature: ambient). Individual standard curves were prepared for each sample tested.

Table 9 shows the total related substances percentage (TRS) formed during the stability testing.

TABLE 9

| Impurity profiles for Tablets A, B and C (storage conditions: 40° C./75% RH). | | | |
| --- | --- | --- | --- |
| Time (weeks) | Tablet A TRS (%) | Tablet B TRS (%) | Tablet C TRS (%) |
| 1 | 0.33 | 0.00 | 0.00 |
| 2 | 0.55 | 0.00 | 0.00 |
| 4 | 1.40 | 0.18 | 0.21 |
| 8 | 2.56 | 0.09 | 0.30 |
| 12 | 3.08 | 0.07 | 0.71 |

The results show that the L-tartrate salt (Example 1, Tablet B) and the L-malate salt (Example 3, Tablet C) possess improved stability in excipients under accelerated storage conditions compared to their respective free base. Furthermore, the results show that the L-tartrate salt (Example 1, Tablet B), possesses improved stability in excipients compared to the L-malate salt (Example 3, Tablet C).

We claim:

1. A compound of the formula:

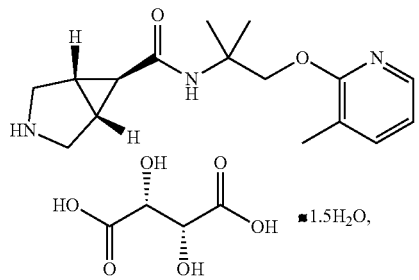

wherein the compound is crystalline and is characterized by an X-ray powder diffraction pattern using CuKα radiation comprising peaks at diffraction angle 2-theta 10.6°±0.2° 15.2°±0.2° and 21.9°±0.2°.

2. A compound of the formula:

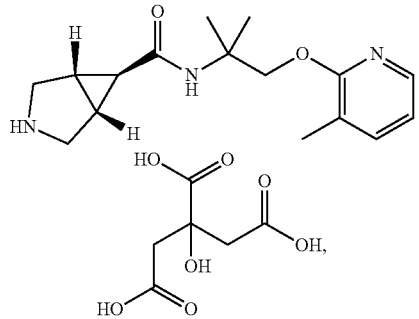

wherein the compound is crystalline and is characterized by an X-ray powder diffraction pattern using CuKα radiation comprising peaks at diffraction angle 2-theta 5.4°±0.2°, 10.3°±0.2°, 16.2°±0.2°, and 20.8°±0.2°.

3. A compound of formula:

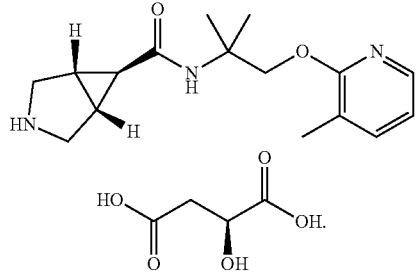

wherein the compound is crystalline and is characterized by an X-ray powder diffraction pattern using CuKα radiation comprising peaks at diffraction angle 2-theta 4.9°±0.2°, 17.3°±0.2°, and 18.1°±0.2°.

4. A pharmaceutical composition comprising the compound of claim 1 and one or more pharmaceutically acceptable carriers, diluents, or excipients.

5. A method of treating pain in a patient comprising administering to said patient in need of such treatment an effective amount of the compound of claim 1.

6. A method of treating chronic back pain in a patient comprising administering to said patient in need of such treatment an effective amount of the compound of claim 1.

7. A method of treating neuropathic pain in a patient comprising administering to said patient in need of such treatment an effective amount of the compound of claim 1.

8. The method of claim 7, wherein the neuropathic pain is diabetic peripheral neuropathic pain.

9. A method of treating pain associated with osteoarthritis in a patient comprising administering to said patient in need of such treatment an effective amount of the compound of claim 1.

10. A method of treating pain in a patient comprising administering to said patient in need of such treatment an effective amount of the compound of claim 2.

11. A method of treating chronic back pain in a patient comprising administering to said patient in need of such treatment an effective amount of the compound of claim 2.

12. A method of treating neuropathic pain in a patient comprising administering to said patient in need of such treatment an effective amount of the compound of claim 2.

13. The method of claim 12, wherein the neuropathic pain is diabetic peripheral neuropathic pain.

14. A method of treating pain associated with osteoarthritis in a patient comprising administering to said patient in need of such treatment an effective amount of the compound of claim 2.

15. A method of treating pain in a patient comprising administering to said patient in need of such treatment an effective amount of the compound of claim 3.

16. A method of treating chronic back pain in a patient comprising administering to said patient in need of such treatment an effective amount of the compound of claim 3.

17. A method of treating neuropathic pain in a patient comprising administering to said patient in need of such treatment an effective amount of the compound of claim 3.

18. The method of claim 17, wherein the neuropathic pain is diabetic peripheral neuropathic pain.

19. A method of treating pain associated with osteoarthritis in a patient comprising administering to said patient in need of such treatment an effective amount of the compound of claim 3.

\* \* \* \* \*